United States Patent [19]

Ghajar et al.

[11] Patent Number: 4,998,938
[45] Date of Patent: Mar. 12, 1991

[54] REMOVABLE SKULL MOUNTED WORK PLATFORM AND METHOD OF ASSEMBLING SAME

[75] Inventors: Jamshid B. G. Ghajar; Fathali G. Ghadjar; Robert J. Hariri, all of New York, N.Y.

[73] Assignee: Neurodynamics, Inc., New York, N.Y.

[21] Appl. No.: 204,451

[22] Filed: Jun. 9, 1988

[51] Int. Cl.$^5$ .............................................. A61B 19/00
[52] U.S. Cl. ..................................... 606/130; 285/206
[58] Field of Search ................. 128/303 B, 305.1, 310, 128/898; 411/41, 55, 60, 384, 397, 160–162; 285/161, 162, 194, 205, 206, 216, 222; 606/130

[56] References Cited

U.S. PATENT DOCUMENTS

| 421,910 | 2/1890 | Dickson | 411/161 |
|---|---|---|---|
| 2,537,183 | 1/1951 | Bloomer | 285/216 |
| 2,664,458 | 12/1953 | Rapath | 411/41 |
| 3,017,887 | 1/1962 | Heyer . | |
| 3,073,310 | 1/1963 | Mocarski . | |
| 4,704,058 | 11/1987 | Crunwell | 411/162 |

FOREIGN PATENT DOCUMENTS

0100185  2/1936  Australia ............................ 285/105

OTHER PUBLICATIONS

Ghajar, A Guide for Ventricular Catheter Placement, J. Neurosurg 63: 985–986 (1985).
Instruction Manual for Ghajar device described in Ref AR.
Cooper, The Neurosurgical Alleviation of Parkensonism, Chemopallidectomy, p. 83 (1956).
Kandall, A Trephine Needle for Vertebral Body Biopsy, the Lancet, Feb. 27, 1960, p. 474.
The Right Angle—pamphlet by Neurodynamics, Inc., Oct. 27, 1987.

*Primary Examiner*—C. Fred Rosenbaum
*Assistant Examiner*—William Lewis
*Attorney, Agent, or Firm*—Pennis & Edmonds

[57] ABSTRACT

A device for facilitating the insertion of an instrument such as a surgical or observational tool into a patient's cranial cavity through a previously formed aperture in the cranium. The device comprises a guide with an open elongated tubular member having a first and a second end, wherein at least a portion of the tubular member at the first and thereof is configured and adapted for passage through the aperture. An outer surface portion of the open tubular member is configured for engagement with a separate locking apparatus for securing the device to the cranial surface. The device further comprises a flanged tip on the first end of the tubular member for stabilizing it within the aperture. An alignment stand configured for the passage therethrough of at least a portion of the device is seated upon the cranium directly above the aperture. The guide is inserted therethrough and into the cranial cavity. Subsequently, an elongated tubular member is inserted into the guide, which spreads the flanged tips therof, thus creating an interference fit between the flanges and the inner surface of the cranium. A locking ring, positioned upon the guide above the alignment stand, is utilized to secure the device against the cranium by screwing the ring in the direction of the stand. A method for assembling the device within a burr hole previously prepared in the patient's cranium is additionally disclosed.

46 Claims, 2 Drawing Sheets

U.S. Patent   Mar. 12, 1991   Sheet 1 of 2   4,998,938

REMOVABLE SKULL MOUNTED WORK PLATFORM AND METHOD OF ASSEMBLING SAME

TECHNICAL FIELD

The invention relates to a surgical working platform, removably mountable within an aperture upon the skull of a patient. More specifically, the device, which is quickly and easily assembled, facilitates insertion and alignment of surgical and observational instruments into the interior of the patient's cranium without causing undue injury to surrounding tissue.

BACKGROUND OF THE INVENTION

Medical personnel practicing in the field of neurosurgery have been aware for a number of years of the importance of penetrating a patient's cranium with surgical tools and instruments at an angle of substantially 90°. The purpose behind this practice is twofold: first, a burr hole drilled at an orientation of 90° to the surface of the skull prevents injury to the underlying dura and brain tissue which may otherwise be caused by the continued rotation of the metal bit of the drilling apparatus once the bit tip exits the bone.

That is to say that, when directed into the skull at an orientation of other than 90°, the bit of drilling devices in current use often continues to rotate after the tip portion has pierced the cranium, despite the incorporation of a standard safety clutch mechanism commonly utilized with such drills. The operation of this standard clutch is such that the drill should automatically stop rotating once the pressure upon the tip is released, i.e., once the tip of the bit passes entirely through the skull bone.

The drill bit commonly utilized in neurological surgical procedures, however, comprises a fixed outer sleeve and a slidable inner sleeve, partially rotatable within the outer sleeve. This inner sleeve extends a short distance beyond the outer sleeve. If the burr hole is oriented at some angle other than 90°, while the trailing edges upon the outer sleeve of the bit are still engaging the bony surface of the patient's skull, the grinding surfaces upon the inner sleeve, which extend beyond those of the outer sleeve as noted above, are quite likely to cause serious injury to the underlying tissue within the cranial cavity.

In contrast, however, a burr hole aligned at an angle of substantially 90° to the surface of the skull permits the clutch mechanism to operate properly and thus stops the rotation of the entire bit once the tip has penetrated the bone, preventing accidental injury to the brain and related tissues within the cranial cavity.

The second and no less important reason for orienting an aperture into the cranial cavity at an angle of substantially 90° to the surface of the skull is to ensure that a surgical tool or instrument which is passed through the aperture and into the underlying tissue of the patient's brain does not deviate from its intended path due to a misaligned skull hole. This feature is particularly important to the success of a number of neurological surgical procedures which include, but which are not limited to such techniques as:

neuroendoscopy;
brain biopsy or stereotactic brain biopsy;
catherization;
placement of brain transplant tissue;
placement of transducers for brain function monitoring; and
the installation of pharmaceuticals within the brain An apparatus and method for ensuring correct placement of, for example, a catheter, within the patient's cranium, has been disclosed and claimed by one of the present applicants in U.S. Pat. No. 4,613,324 issued Sept. 23, 1986. This apparatus, when positioned over an orifice (previously drilled by other means) above the anterior horn of the lateral ventricle of the brain, guides a catheter with its attendant obdurator through the orifice and into the lateral ventricle at an angle normal to a plane formed by a tangent to the cranium at the orifice.

The device comprises a tubular member which is adapted to receive and guide the catheter through the burr hole in the patient's cranium, having a support which is adapted to rest unsecured upon the cranium in surrounding spaced relation to the orifice. The support and the tubular member are spatially related so as to guide the catheter through the orifice in a direction perpendicular to an imaginary plane defined by a tangent to the cranium at the orifice. The tubular member thus serves to guide the remainder of the catheter when the free end thereof is inserted into the patient's brain.

There is, however, no prior art of which applicants are aware that discloses any apparatus or device capable of properly orienting all of the various surgical and observational instruments which are utilized in the various neurological procedures outlined above. The need for such a device has thus led to a search for an easily assembled working platform which facilitates access to a particular location within the brain of a patient without the occurrence of what may now be characterized as unnecessary trauma to the surrounding tissue.

SUMMARY OF THE INVENTION

It is therefore an object of the present invention to provide a work platform which permits access to the interior of a patient's cranium through a burr hole drilled in the overlying cranial bone while limiting the size of the required incision and the amount of bone removed.

Another object of the device described herein is to minimize contact by instruments and tools with the patient's scalp and cranium during the surgical procedure, thus reducing the risk of infection to the surrounding tissue.

A further object of the invention is to provide work platform mounted in a burr hole on the skull for use in various neurological surgical procedures, having alignment markings along an upper surface thereof which are visible to the surgeon during the operation, to assist in orienting the instruments utilized during the surgery relative to outside markings on the patient's skull or X-rays or other views of the interior of the patient's cranium.

A still further application of the device described herein is to provide a work platform secured at a substantially perpendicular angle to the patient's skull. Thus, any instrument or device passed through the lumen of the platform will enter the cranium at an angle of substantially 90° to a plane tangent to the skull at the aperature, thereby avoiding any unnecessary trauma to the brain.

The surgical work platform of the present invention is designed to be quickly and easily mounted in a burr hole drilled in the cranium for that purpose and just as easily disassembled upon completion of the required surgical procedure.

The apparatus disclosed and claimed herein thus comprises a platform for facilitating the insertion of an instrument such as a surgical tool or an observational device through a burr hole previously formed in the patient's cranium. The platform comprises guide means for directing the instrument through the burr hole. The guide means comprises an elongated open tubular member with a first end, a second end, and a lumen extending from the first end to the second end, wherein at least a portion of the tubular member at the first end is configured and adapted to pass through the burr hole and into an inner part of the cranium. Moreover, at least a portion of the outer surface of the tubular member is threaded for engagement with separate locking means.

The guide means additionally comprises a flexible tip portion for stabilizing the device within the burr hole. This tip portion is formed integral with the first end of the tube, on a terminal portion thereof, and comprises a plurality of flexible slotted members, each having an outwardly extending substantially horizontal flange at the end thereof furtherest removed from the tube.

In addition, the guide means further comprises a body portion formed integrally with the tube at the second end thereof. The body portion has upper and lower opposed surfaces, the lower one of which is adjacent and formed integral with the tubular member. The body portion defines a central lumen adjacent to and in communication with that of the tubular member, extending entirely therethrough, which forms an uninterrupted open bore within the base of the device. That segment of the bore defined by the body portion is threaded to engage corresponding threads upon an outer surface of an insert member to lockingly engage the insert within the guide.

Moreover, located on the upper surface of the body portion are markings for aligning instruments passing though the device with a point outside the cranium. These marks may be, for example, molded, etched or painted on this upper surface. The presence of these alignment marks thus enables the surgeon to more readily line up the instrument with the point in the underlying brain tissue which is the object of the surgery.

An additional component of the device is an alignment stand, having a ring shaped body portion and a plurality of leg members extending substantially perpendicularly therefrom. This stand is placed upon the patients' cranium directly above the burr hole. The free ends of the leg members define a plane upon the cranium which lies at a tangent of substantially 90° to the burr hole.

A locking ring, having first and second opposed parallel surfaces, defines a central lumen therethrough which is threaded for engagement with the corresponding threads located on the outer surface of the tubular member. The central lumen of the locking ring is sized to accept the tubular member and these components are thus screwed together during assembly of the device.

The final component of the platform is an elongated tubular insert member having a first end and a second end and defining a central lumen extending from the first end to the second end. The second end of the insert member is provided with threads on an outer surface thereof configured to engage the corresponding threads on an inner surface of that portion of the bore formed by the body portion.

During assembly of applicants' surgical working platform, a burr hole is prepared in the patient's cranium with perforation means such as a manual, electrical or hydraulically operated drill. The alignment stand is thereafter placed over the burr hole after the aperture has been deburred to remove any loose bone chips. The legs which support the body portion of the stand each terminate in a free end, which free ends define a plane on the patient's cranium at an orientation of substantially 90° to the burr hole.

The locking ring is thereafter screwed onto the tubular member of the platform and the tip portion thereof is inserted through the body of the alignment stand and into the patient's cranium. Once the tip is passed through into the cranial cavity, the elongated tubular insert member is placed into the bore of the platform. The lower portion of the insert, upon passing through the lumen defined by the tip members, spreads these members apart due to its relatively greater diameter. As they are spread, the flanged portions located at the end of each member contact the inner surface of the cranium. Subsequently, the locking ring is screwed downwardly on the tubular member, i.e. toward the cranium, into a position near or in contact with the alignment stand. The tension caused by the tightening of the locking ring results in the flanged portions of the ring member being moved upwardly against the inner surface of the skull so as to lock the working platform into position for use.

Once the surgery is completed, the platform may be disassembled by unscrewing the locking ring away from the patient's cranium, removing the insert from its position within the bore and withdrawing the device out of the burr hole in the patient's cranium. The removal of the platform, however, does not necessarily require the removal of all of the surgical and/or other medical tools or instruments passed therethrough into the patient's cranium. For example, a catheter guided into the anterior horn of the patient's lateral ventricle could be left in position, undisturbed within the cranial cavity even after the surgical platform was disassembled and removed.

DETAILED DESCRIPTION OF THE PREFERRED EMBODIMENTS

Figure 1:
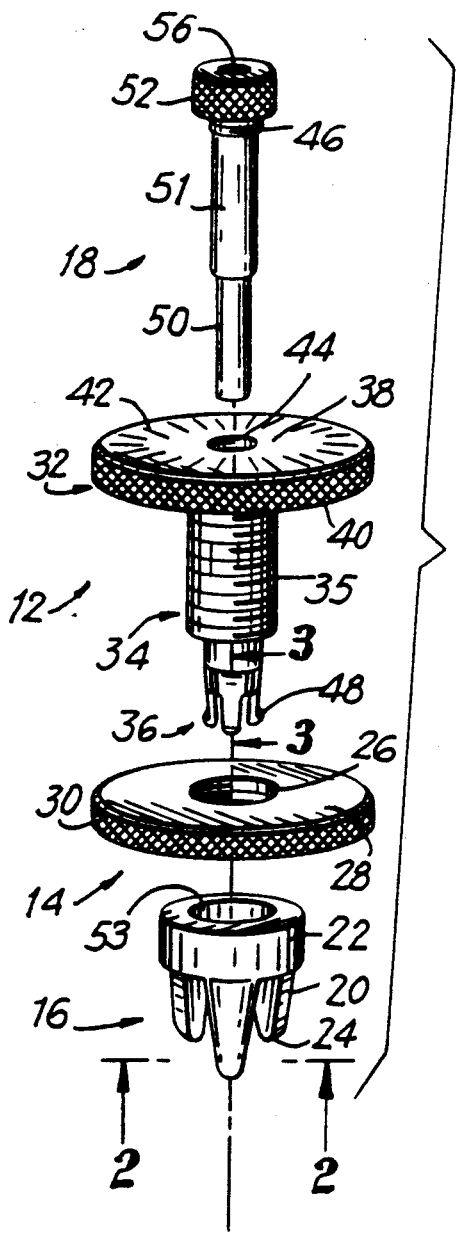
FIG. 1 is an exploded view of applicants' cranial work platform.

Referring initially to FIG. 1, there is illustrated an exploded view of applicants' cranial work platform 10. Platform 10 is comprised of a number of interlocking component parts, including base 12, which is configured to extend through a central lumen defined by tension nut 14 and compression stand 16, thus facilitating the insertion of tip portion 36 of base 12 through to the inner surface of the patient's skull. Insert 18 is thereafter secured within a hollow central bore formed within base 12 to complete the assembly of platform 10. The various component parts described above are preferably formed of a metal or by molding from an engineering thermoplastic such as Delrin®, ABS, an acrylic, resin etc.

Base 12 is constructed with three segments, i.e., disc-shaped body portion 32, hollow tubular member 34 extending downwardly from a lower surface of body 32 and formed integrally therewith and tip 36 formed upon a lower terminal portion (i.e., that portion closest to the patient's cranium) of tubular member 34. Body 32 is comprised of upper 38 and lower 39 opposed parallel surfaces joined along their peripheral circumferential edges by side wall 40. Wall 40 is preferably cross-hatched or corrugated to facilitate gripping by the surgeon.

Located upon upper surface 38 of body 32 are alignment marks 42. These marks are preferably molded or painted along the outer circumferential periphery of upper surface 38 for the purpose of orienting the direction of instruments inserted by the surgeon into the patient's cranial cavity relative to reference points on the outside of the skull, or to X-rays or other pictures taken of the interior of the cranium. In a preferred embodiment of the invention, the marks are located 15° apart from one another, but this spacing is not critical. The distance between these marks may thus be varied as required for particular applications.

Body 32 further defines a hollow central lumen extending therethrough, from the upper surface 38 to the lower surface 39 thereof, in alignment with and adjacent to a similarly aligned lumen defined by tubular member 34 and tip 36. These lumens thus form a hollow central bore passing entirely through base 12 from upper surface 38 of body 32 to the terminus of tip 36. Threads 44 are molded along the inner peripheral wall of the lumen in body 32 for the purpose of engaging corresponding threads on the outer portion of insert 18 when platform 10 is assembled.

Tubular member 34 is formed integral with lower surface 39 of body 32 and extends downwardly therefrom in a substantially perpendicular orientation. Member 34 is provided with threads 35 molded into the outer wall thereof for engagement with corresponding threads 26 located within the lumen of tension nut 14. In addition, tubular member 34 terminates in a slotted, flanged tip 36 which is configured and dimensioned for passage through a lumen in both tension nut 14 and compression stand 16 and thereafter through a previously drilled burr hole in the cranium of the patient.

Tip 36 is of a reduced diameter from the remainder of tubular member 34. It is capable of a limited degree of flexibility due to its slotted construction. Flanges 48 are perpendicularly oriented at a terminal portion of each tip member 36 a-d to engage an inner surface of the patient's skull once tip 36 is passed through the burr hole and into the patient's cranial cavity.

Insert 18 is configured to pass through the hollow central bore in base 12. It is configured in the shape of an elongated tube which defines an inner lumen 56 extending from one end to the other. As insert 18 passes through this bore, threads 46 on an upper outer portion of the insert engage the corresponding threads 44 located within the lumen of body portion 32 to lock insert 18 into position in the bore of base 12. The lower terminal portion 50 of insert 18 has a reduced diameter from the remainder 51 of insert 18 to enable it to pass through the smaller bore of tip 36 (i.e., smaller in relation to the rest of tubular member 34). Thus, as the lower portion 50 of insert 18 passes downwardly through tip 36, portion 50 thus presses outwardly against the flexible, slotted members a-d of tip 36 to force them outwardly and thus lock flanges 48 against the inner surface of the skull as described above.

The upper terminal portion 52 of insert 18 is configured in the form a ring, preferably having a cross-hatched or corrugated outer surface, to facilitate gripping by the surgeon when screwing insert 18 into base 12. Insert 18 is formed in the shape of an elongated tube and thus defines a hollow lumen extending therethrough, configured for the passage of surgical and observational instruments in common use during a variety of neurological procedures.

Compression stand 16, which serves to align platform 10 within the burr hole in the cranium, comprises a ring shaped body portion 22 having an aperture 53 therethrough, supported upon a plurality of leg members 20, preferably three in number. The legs are formed integral with and extend substantially perpendicularly from a lower surface of ring shaped body portion 22. Each leg member 20 terminates in a free end 24, which free ends 24 form a polygon upon the surface of the patient's cranium, thus defining a plane.

Tension nut 14 is anularly configured, having upper 28 and lower opposed parallel surfaces. Nut 14 is provided with threads 26 within a central lumen defined thereby, which threads 26 are configured to engage corresponding threads 35 molded on the outer surface of tubular member 34. Both upper 28 and lower parallel surfaces of tension nut 14 may be smooth, whereas the peripheral, circumferential surface 30 of nut 14 is preferably cross-hatched or corrugated in a manner similar to side wall 40 on body portion 32 of base 12 to facilitate gripping by the surgeon.

Figure 2:
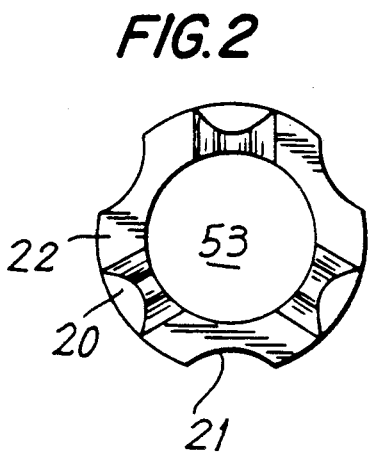
FIG. 2 is a sectional view taken through line 2—2 of FIG. 1.

Turning now to FIG. 2, there is illustrated the lower surface of compression stand 16. As shown in this view, hollow ring portion 22 has a plurality of supporting leg members 20 formed integral therewith and extending substantially perpendicularly therefrom. Moreover, ring portion 22 is formed with notches 21 along the edges thereof to facilitate gripping by the surgeon while the remainder of platform 10 is inserted through aperture 53 in stand 16 and stabilized against the patient's cranium by perpendicular flanges 48 located on slotted tip members 36 a-d.

Figure 3:
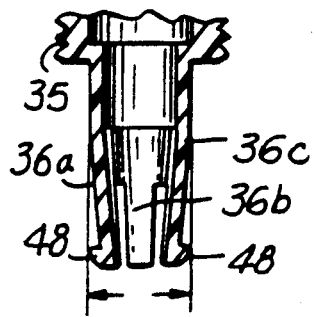
FIG. 3 is a sectional view taken through line 3—3 of FIG. 1.

FIG. 3 is a sectional view of tip 36 located at the lower terminal portion of tubular member 34 and formed integrally therewith. Tip 36 is formed with a number, preferably four, of slotted projecting members 36a-d (36d is not visible). Each such member is provided with a flange 48 at the end thereof to assist in stabilizing platform 10 within the burr hole in the patient's cranium. Projecting members 36a-d are somewhat flexible, i.e., they are capable of a limited degree of inward compression and/or outward expansion toward or away, respectively, from a central vertical axis passing through the portion of the hollow lumen defined by tip 36. This flexibility permits tip 36 to be compressed to a sufficient degree so as to permit the entry of base 12 into the cranial cavity through a previously prepared burr hole. It additionally facilitates and allows subsequent locking engagement between flanges 48 and the inner surface of the patient's skull once the insert 18 is positioned within the bore of base 12. Additional details concerning the preferred method of assembly and use of platform 10 will be provided below.

Figure 4:
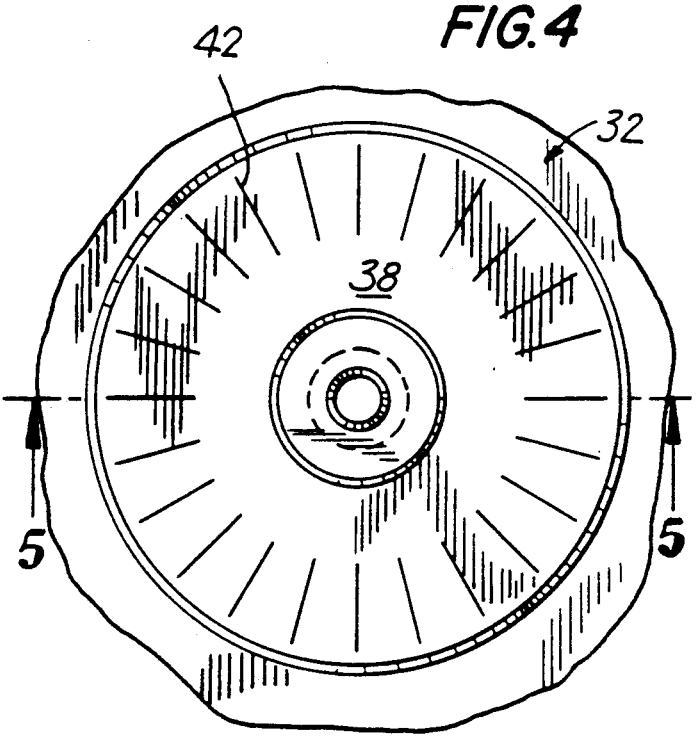
FIG. 4 is a top plan view of applicants' device.

FIG. 4 is a top plan view of body portion 32 on base 12. As noted above, insert 18 is screwed into position within the central lumen in base 12 by the engagement of threads 44, 46 molded on the body 32 and the insert 18 respectively. Alignment marks, preferably molded or painted upon the upper surface 38 of body 32, serve to facilitate the orientation of surgical and/or observational instruments within the skull once these instruments are passed through platform 10. This alignment function serves a two-fold purpose, i.e., first, to enable the surgeon to reach a particular portion of the brain without undue probing and, secondly, to prevent such probing from causing unnecessary injury or trauma to adjacent tissues underlying the burr hole.

A particular mark 42 may, for example, be lined up relative to a point upon the outer surface of the patient's skull, subsequent to which one of a number of instruments required for a particular medical procedure would be passed through platform 10 and into the cranial cavity in a corresponding alignment. Thereafter, as body 32 of base 12 is rotated around its axis, the angular deflection of the instrument from the original starting point is instantly known. Thus, the placement and orientation of such instruments within the skull is facilitated and unnecessary trauma to surrounding tissue caused due to excessive manipulation of the instrument is eliminated.

Figure 5:
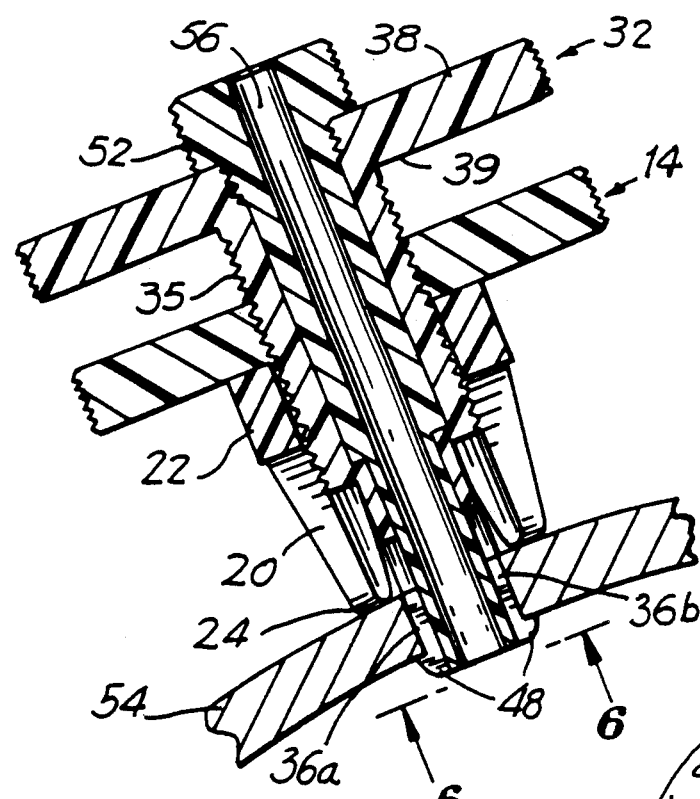
FIG. 5 is a sectional view taken through line 5—5 of FIG. 4.

FIG. 5 illustrates the mode of interconnection between the various components of the device when platform 10 is fully assembled. Prior to installing platform 10 upon the patient's cranium 54, the bone of the skull is penetrated by the surgeon with a perforator of the type commonly used in such surgical procedures. The hole in cranium 54 is then deburred to ensure that there are no bone chips which might subsequently pass through the burr hole and injure the patient's brain.

Compression stand 16 is thereafter centered over the open burr hole and base 12 is inserted through the lumen of tension nut 14 and through aperture 53 in stand 16 so that the slotted, flanged tip portion 36 of base 12 passes through the burr hole to the inner table of cranium 54. Insert 18 is then passed through the bore defined by body 32 and tubular member 34 of base 12, where it is locked into place by engaging threads 44, 46. This action forces the slotted, flanged tip members 36 a-d of base 12 to be pushed outwardly, by the lower portion 50 of insert 18, whereupon flanges 48 engage the inner table of cranium 54. Platform 10 is thereafter stabilized upon the patient's cranium by screwing down, i.e., toward the patient's cranium, on tension nut 14, thus forcing compression stand 16 against the skull, where it is maintained in position by the engagement between tip members 36 a-d and the inner surface of the patient's cranium 54.

What is thus formed is a surgical working platform 10 defining a continuous central lumen 56 configured for the passage of various surgical and observational tools and/or instruments into the patient's cranial cavity. After the surgical procedure has been completed, insert 18 is unscrewed and withdrawn from base 12, thus permitting flexible tip portions 36 a-d to return to their original unexpanded configuration, after which, upon loosening tension nut 14 by unscrewing it away from the patient's cranium, the remainder of platform 10, including compression stand 16, may be removed.

Figure 6:
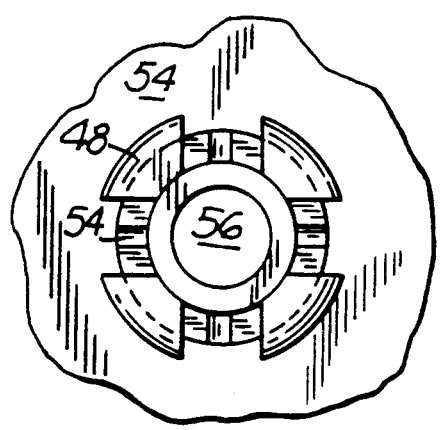
FIG. 6 is a sectional view taken through line 6—6 of FIG. 5.

FIG. 6 is a sectional view taken through tip portion 36 of base 12. The flanges 48 by which the flexible, slotted portions a-d of tip 36 are locked into position upon the inner table of cranium 54 are clearly illustrated. As noted above, when lower portion 50 of insert 18 is pushed through tip 36, the tip members are forced outwardly to accommodate this passage. Grooves 58, located between each tip member 36 a-d permit the required degree of flexibility. Upon assembly of platform 10, the upper surfaces of flanges 48 rest against the inner table cranium 54, thus preventing vertical movement by platform 10, while permitting rotation around a vertical axis passing through bone 56.

Figure 7:
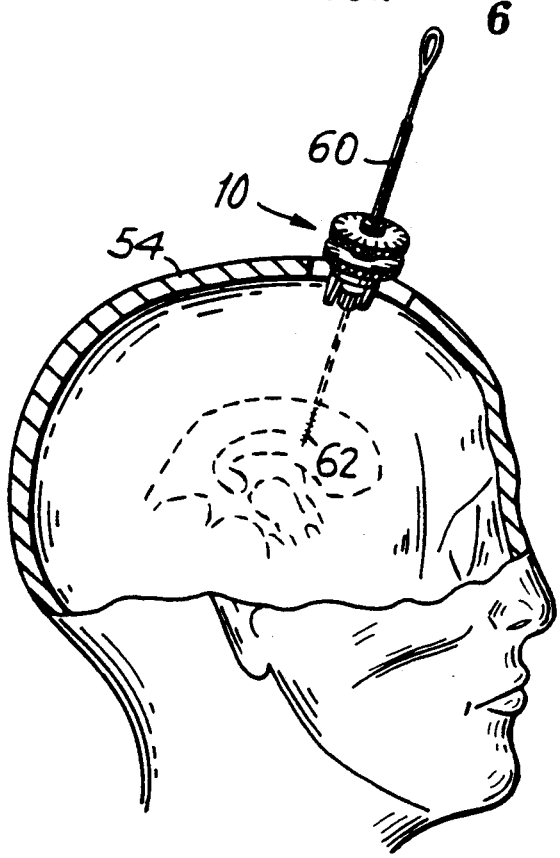
FIG. 7 is a view, partially in section, of applicants' cranial work platform as it is utilized to guide a catheter perpendicularly into the lateral ventricle of a patient's brain.

FIG. 7 displays a side view of platform 10 as it is utilized to insert, for example, catheter 60 through the surface of cranium 54 and into the anterior horn of lateral ventricle 62 of the brain. It is particularly important, as discussed in detail above, that catheter 60 access the ventricular system of the brain at an angle of substantially 90° because the brain columns within the cranial cavity are known to radiate an at angle of 90° from the ventricle. Thus, this orientation facilitates the passage of a tool or an instrument such as catheter 60 through platform 10 and into ventricle 62 with a minimal amount of damage to the surrounding tissue.

A number of additional advantages may be realized with the use of the presently disclosed platform 10 which include, but which are not limited to:
- the establishment of a surgical work platform 10 located away from the outer surface of skull 54, thus preventing undue contact with the surrounding tissue and reducing the chance of injury or infection;
- providing graduated alignment marks 42 upon the upper surface 38 of body portion 32 of the platform, which may be utilized by the surgeon to orient the direction of the tools and/or instruments inserted within the cranial cavity;
- eliminating the need for drilling multiple burr holes into the skull 54, i.e., the platform 10 is mounted directly on the hole which is used for passing instruments into the cranial cavity;
- providing a working platform 10 that can be easily installed and removed without damage to the surrounding bone or tissue; and
- configuring the device to facilitate quick and inexpensive manufacturing, thus enabling platform 10 to be offered as a sterile, disposable item which is utilized during a single surgical procedure and then discarded.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. A device for facilitating the insertion of an instrument into the cranium of a patient through an aperture previously formed in said cranium, without causing undue injury to underlying tissue therein, said device comprising:
   a. guide means disposed in said aperture for directing said instrument through said aperture, said guide means comprising
      i. an elongated open tubular member having a first end and a second end, said member defining a lumen extending from said first end to said second end, wherein at least a portion of said member at said first end is configured for passage through said aperture and into an inner portion of said cranium;

ii. means formed integral with said open tubular body member, at said first end thereof, for stabilizing said guide means within said aperture in said cranium; and iii. a body portion having first and second parallel opposed sides, said first side of said body portion formed integral with said elongated open tubular member at said second end thereof, said body portion defining a lumen extending therethrough from said first side to said second side, in alignment with and adjacent to said lumen in said tubular member, to form, in combination therewith, an uninterrupted bore through said guide means;

b. adjustable means for locking said guide means against said cranium, said locking means defining an aperture therethrough, and configured and adapted for engaging said outer surface portion of said tubular member; and c. a base member for aligning said guide means within said aperture in said cranium, said base member having an annular body portion with first and second opposed sides and a plurality of leg members extending substantially perpendicularly from said first side thereof, said leg members formed integral with said body portion, said base member being configured for the passage therethrough of at least a portion of said guide means, wherein instruments inserted through said device enter the interior of the cranium at an angle of substantially 20° to a plane tangent to the cranium at the aperture.

2. The device of claim 1 wherein said lumen defined by said body portion has thread means located along an inner peripheral circumferential portion thereof, said thread means positioned to engage corresponding thread means on an elongated insert member positionable within said uninterrupted bore.

3. The device of claim 2 further comprising an elongated tubular insert member having a first end and a second end and defining a hollow lumen extending from said first end to said second end, at least a portion of said insert member adjacent said first end thereof being configured for passage substantially through said uninterrupted bore through said guide means.

4. The device of claim 3 wherein said insert member further comprises thread means located on an outer surface thereof adjacent said second end, wherein said thread means on said insert member are configured for engagement with corresponding thread means within said lumen of said base body portion so as to lockingly position said insert member within said uninterrupted bore through said guide means.

5. The device of claim 1 wherein said second side of said body portion comprises a plurality of marking means to facilitate alignment of said instrument within said cranium upon the insertion thereof through the lumen of said guide means.

6. The device of claim 5 wherein said marking means are each located the same distance apart from one another along a peripheral circumferential portion of said second side of said body portion.

7. The device of claim 6 wherein each said marking means is located 15 degrees apart from either adjacent one of said marking means.

8. The device of claim 1 wherein said stabilizing means comprises a plurality of flexible slotted tip members formed integral with said open tubular member at a first terminal portion thereof, each said tip member having a flange extending outwardly from a terminal portion thereof furtherest removed from said open tubular member.

9. The device of claim 8 wherein said flanges extend outwardly in a substantially perpendicular direction from each said tip member and are formed integral therewith.

10. A method for inserting a medical instrument through a previously prepared aperture in a patient's cranium, said method comprising:

a. assembling the device of claim 1 upon the cranium of a patient by
  1. forming an aperture through said cranium at an angle of substantially 90° to a plane tangent to the cranium at the aperture;
  2. deburring the aperture to remove any loose bone chips therefrom;
  3. positioning said base member above said aperture on the surface of the cranium;
  4. inserting said guide means through said aperture on the surface of the cranium; and
  5. engaging an elongated insert member having a central lumen within an uninterrupted bore defined by said guide means; and b. inserting said medical instrument through said device and into an interior portion of said cranium at an angle of substantially 90° to a plane tangent to said cranium at said aperture.

11. A surgical work platform for facilitating insertion of an instrument into the cranium of a patient through a burr hole previously formed in said cranium, without causing undue injury to underlying tissue therein, said platform comprising:

a. a guide disposed in said aperture for directing the instrument through the burr hole, said guide comprising
  i. an elongated open tubular member having a first end and a second end, said member defining a lumen extending from said first end to said second end, wherein at least a portion of said member at said first end is configured for passage through said aperture and into an inner portion of said cranium and wherein at least a portion of an outer surface of said member is threaded for engagement with separate locking means;
  ii. a body portion having first and second parallel opposed sides, said first side of said body portion formed integral with said elongated tubular member at said second end thereof, said body portion defining a central lumen extending therethrough from said first side to said second side in alignment with and adjacent to said lumen in said tubular member so as to form, in combination therewith, an uninterrupted bore through said guide, wherein said lumen extending through said body portion has a plurality of thread members located along an inner peripheral circumferential portion thereof to engage corresponding thread member located upon an insert member positionable within said bore; and iii. a plurality of flexible slotted tip members formed integral with said elongated open tubular member at a terminal portion of said first end thereof, for stabilizing said guide within the burr hole in the patient's cranium, each said tip member having a substantially perpendicular flange extending outwardly from a terminal portion thereof furtherest removed from said open tubular member;

b. adjustable locking means for securing the guide against the patient's cranium, said locking means defining a central lumen configured for engaging said threaded outer portion of said elongated open tubular member;

c. an elongated tubular insert member having a first end and a second end, said insert member defining a hollow lumen extending from said first end to said second end, wherein at least a portion of said insert member adjacent said first end thereof is configured for passage substantially through said uninterrupted bore of said guide, and wherein said insert member has a plurality of thread members on an outer surface thereof adjacent said second end, said thread members corresponding to said thread members within the lumen of said body portion for lockingly positioning the insert member within the bore of the guide; and d. a base member for aligning the guide within the burr hole in the patient's cranium, said base member having an annular body portion with first and second opposed sides and a plurality of leg members extending substantially perpendicularly from said first side thereof, said leg members formed integral with said body portion, said base member being configured for the passage therethrough of at least a lower portion of said guide so as to permit engagement of said guide within said burr hole, wherein an instrument inserted through said platform enters the interior of the patient's cranium at an angle of substantially 90° to a plane tangent at the cranium at the burr hole.

12. The platform of claim 11 wherein the second side of said body portion comprises a plurality of graduated alignment markings located along a peripheral circumferential portion thereof, each said marking being located about 15 degrees apart from an adjacent marking on either side thereof.

13. The platform of claim 11 wherein at least the first end portion of said insert member has a correspondingly greater diameter than that of said flexible, slotted tip members such that passing said insert member through said uninterrupted bore in said guide and thereafter between said tip members, forces said tip members outwardly, away from said insert member, facilitating a secure engagement between said perpendicular flanges located upon said tip members and an inner surface of the patient's cranium, thus enhancing the stability of the platform.

14. The platform of claim 11 wherein said locking means comprises a ring-shaped member having upper and lower parallel opposed surfaces, defining a central aperture therethrough, extending from said upper surface to said lower surface, said aperture having threaded members located on an inner peripheral surface thereof for engaging said corresponding threaded members located upon the outer surface portion of said elongated open tubular member, thus permitting said platform to be locked in position upon the cranium of the patient by screwing said ring-shaped member in the direction of said alignment means.

15. The platform of claim 14 wherein each of said plurality of legs terminates in a free end, said free ends forming a polygon defining a plane upon said cranium overlaying said burr hole and wherein said guide is aligned with the burr hole at an angle of substantially 90° to said plane.

16. The platform of claim 15 wherein said base member comprises three legs of equal length such that an equilateral triangle is formed by the free ends of said legs.

17. The platform of claim 11 wherein said guide, said insert and said alignment means are constructed from a rigid material comprising ABS, Delrin ®, Hetal or an acrylic.

18. A skull-mounted surgical work platform for facilitating the insertion of medical instruments into the cranium of a patient through a burr hole previously formed in said cranium without causing undue injury to underlying tissue therein, said platform comprising:

a. a guide for directing said instruments through the burr hole, said guide comprising
i. an elongated open tube having a first end and a second end, said tube defining a central lumen extending therethrough from said first end to said second end, wherein at least a portion of an outer surface thereof is threaded for engagement with a separate locking ring;
ii a body portion having first and second parallel opposed sides, said first side of said body portion formed integral with said elongated open tube at the second end thereof and said second side of said body portion having a plurality of graduated alignment markings along a peripheral circumferential portion thereof, each said marking being located substantially 15° apart from an adjacent marking on either side thereof, said body portion further defining a central lumen extending therethrough from said first side to said second side in alignment with and adjacent to said lumen of said tube to form, in combination therewith, an uninterrupted bore through said guide and wherein said lumen extending through said body portion has threads located along a peripheral circumferential portion thereof to engage corresponding threads located upon an insert member positionable within said bore;
iii. a plurality of flexible slotted tip members formed integral with said tube at a terminal portion of said first end thereof for stabilizing said guide within the burr hole in the patient's cranium, each said tip member having a substantially perpendicular flange extending from a terminal portion thereof furtherest removed from said tube;

b. an elongated tubular insert member with a first end and a second end, having a hollow lumen extending from said first end to said second end, wherein at least a portion of said insert member adjacent said first end thereof is configured for passage substantially through said uninterrupted bore of said guide, and wherein said insert member has threads on an outer surface thereof adjacent said second end, said threads configured for engagement with corresponding threads within the lumen of said body portion to lockingly position the insert within the bore of the guide and further wherein at least the first end portion of the insert member has a correspondingly greater diameter than that of said flexible slotted tip members, such that passing said insert member through said bore, and thereafter between said tip members, forces said tip members outwardly, away from said insert member, thus facilitating a secure engagement between said flanges upon said tip members and an inner surface portion of the patient's cranium;

c. a ring-shaped locking member having upper and lower parallel opposed surfaces and defining a central lumen therethrough, said lumen extending from said upper to said lower surface, wherein said lumen has threads on an inner surface thereof for engaging corresponding threads located upon the outer surface portion of the elongated open tube, thus permitting the platform to be locked in position on the patient's cranium by screwing the locking member toward the patient's cranium; and d. a base member for aligning said platform within said burr hole, said base member comprising an annular body portion with first and second opposed sides, and having three leg members extending substantially perpendicularly from said first side, wherein each said leg member terminates in a free end, said free ends forming a triangular plane on the surface of the patient's cranium overlaying said burr hole such that said tube is aligned with said burr hole through said triangular plane at an angle of substantially 90° to said plane.

19. A method for assembling a skull mounted work platform upon the cranium of a patient, which comprises:

a. forming an aperture through said cranium at an angle of substantially 90° to a plane tangent to the cranium at the aperture;

b. deburring the aperture to remove any loose bone chips therefrom;

c. positioning alignment means above said aperture on the surface of the cranium;

d. inserting guide means through said alignment means and thereafter through said aperture into an interior portion of said cranium;

e. engaging an elongated insert member having a central lumen within an uninterrupted bore defined by said guide means; and f. passing a medical instrument through the lumen of said insert member to enable said instrument to penetrate an underlying portion of said patient's brain at an angle of substantially 90° thereto, so as to prevent undue injury to tissue within the cranium underlying said aperature.

20. The method of claim 19 wherein said aperture is formed by drilling through said cranium with the perforator means at an angle of substantially 90° to a plane tangent to said cranium at said aperture.

21. The method of claim 20 wherein said drilling may be performed manually, pneumatically electrically or hydraulically.

22. The method of claim 19 wherein an upper portion of said insert member is lockingly engaged within the uninterrupted bore of said guide means by engaging corresponding male and female thread means located, respectively, on an outer surface of said insert member and on an inner peripheral surface of said bore.

23. The method of claim 19 wherein said guide means is engaged against an inner surface of said cranium by spreading a plurality of tip members located at a first terminal end of said guide outwardly by passing therebetween said insert member, such that as a result of said expansion, perpendicularly extending flanges, located at a terminal portion of each said tip member, engage a portion of the inner surface of said cranium adjacent said aperture.

24. The method of claim 19 which further comprises securing said work platform in position within said aperture by engaging locking means located on said platform.

25. The method of claim 24 wherein said locking means are engaged by screwing a locking ring positioned upon said guide means, toward said alignment means on the surface of said cranium.

26. A device for facilitating the insertion of an instrument into the cranium of a patient through an aperture previously formed in said cranium, without causing undue injury to underlying tissue therein, said device comprising:

guide means disposed in said aperture for directing said instrument through said aperture, said guide means comprising an elongated open tubular member having a first end and a second end, said member defining a lumen extending from said first end to said second end, and a body portion having first and second parallel opposed sides, said first side of said body portion formed integral with said elongated tubular member at said second end thereof, said body portion defining a central lumen extending therethrough from said first side to said second side in alignment with and adjacent to said lumen in said tubular member so as to form, in combination therewith, an uninterrupted bore through said guide means, wherein at least a portion of said member at said first end is configured for passage through said aperture and into an inner portion of said cranium without causing undue injury to underlying tissue therein, said guide means further comprising a base member having an annular body portion with first and second opposed sides, a central aperture therein, and a plurality of leg members extending substantially perpendicularly from said first side thereof, said leg members formed integral with said body portion; and means for aligning said guide means within said aperture in said cranium, said alignment means including a tubular member configured for passage through at least a portion of said guide means and having a first end which is operatively associated with the first end of the guide means so that when inserted therein, said tubular member positions, aligns and locks said guide means in said cranium aperture;

wherein instruments inserted through said device enter the interior of the cranium at an angle of substantially 90° to a plane tangent to the cranium at the aperture.

27. The device of claim 26 wherein said stabilizing means comprises a plurality of flexible slotted tip members formed integral with said open tubular member at a first terminal portion thereof, each said tip member having a flange extending outwardly from a terminal portion thereof furtherest outwardly from a terminal portion thereof furtherest removed from said open tubular member.

28. The device of claim 27 wherein said flanges extend outwardly in a substantially perpendicular direction from each said tip member.

29. The device of claim 26 which further comprises means for securing said base member to said cranium.

30. The device of claim 29 wherein the securing mens comprises a disc member having a threaded central aperture therein for engagement with a threaded outer portion located on said guide means in a manner such that said support member is held against said cranium.

31. The device of claim 26 wherein said alignment means tubular member includes means for releasably engaging said guide member for attachment thereto.

32. The device of claim 31 wherein said releasable engaging means comprises a threaded area of said guide means lumen located adjacent said second end and a threaded area of said alignment means located at an outer portion of an end opposite said first end.

33. A device for facilitating the insertion of an instrument into the cranium of a patient through an aperture previously formed in said cranium, without causing undue injury to underlying tissue therein, said device comprising:
   a. guide means for directing said instrument through said aperture, said guide means comprising
      i. an elongated open tubular member having a first end and a second end, said member defining a lumen extending from said first end to said second end, wherein at least a portion of said member at said first end is configured and adapted for passage through said aperture and into an inner portion of said cranium;
      ii. means formed integral with said open tubular member, at said first end thereof, for stabilizing said guide means within said aperture in said cranium; and
      iii. a body having first and second parallel opposed sides, said first side of said body portion formed integral with said elongated open tubular member at said second end thereof and said second side of said body portion comprising a plurality of marking means to facilitate alignment of said instrument within said cranium, said body portion defining a lumen extending therethrough from said first side to said second side, in alignment with an adjacent to said lumen in said tubular member, to form in combination therewith, an uninterrupted bore through said guide means; and
   b. adjustable means for locking said guide means against said cranium, said locking means defining an aperture therethrough, configured and adapted for engaging said tubular member; and
   c. means for aligning said guide means within said aperture in said cranium, said alignment means configured for the passage therethrough of at least a portion of said guide means,
   wherein instruments inserted through said device enter the interior of the cranium at an angle of substantially 90° to a plane tangent to the cranium at the aperture.

34. The device of claim 33 wherein said marking means are each located the same distance apart from one another along a peripheral circumferential portion of said second of said body portion.

35. The device of claim 34 wherein each said marking means is located 15 degrees apart from either adjacent one of said marking means.

36. A surgical work platform for facilitating insertion of an instrument into the cranium of a patient through a burr hole previously formed in said cranium, without causing undue injury to underlying tissue therein, said platform comprising:
   a. guide for directing the instrument through the burr hole, said guide comprising
      i. an elongated open tubular member having a first end and a second end, said member defining a lumen extending from said first end to said second end, wherein at least a portion of said member at said first end is configured and adapted for passage through said aperture and into an inner portion of said cranium;
      ii. a body portion having first and second parallel opposed sides, said first side of said body portion formed integral with said elongated tubular member at said second end thereof and said second side of said body portion comprising a plurality of graduated alignment markings located along a peripheral circumferential portion thereof, each said marking being located about 15 degrees apart from an adjacent marking on either side thereof, said body portion defining a central lumen extending therethrough from said first side to said second side in alignment with and adjacent to said lumen in said tubular member so as to form, in combination therewith, an uninterrupted bore through said guide, wherein said lumen extending through said body portion has a plurality of thread members located along an inner peripheral circumferential portion thereof to engage corresponding thread members located upon an insert member positionable within said bore; and
      iii. a plurality of flexible slotted tip members formed integral with said elongated open tubular member at a terminal portion of said first end thereof, for stabilizing said guide within the burr hole in the patient's cranium, each said tip member having a substantially perpendicular flange extending outwardly from a terminal portion thereof furtherest removed from said open tubular member;
   b. adjustable locking means for securing the guide against the patient's cranium, said locking means defining a central lumen configured for engaging said elongated open tubular member;
   c. an elongated tubular insert member having a first end and a second end, said insert member defining a hollow lumen extending from said first end to said second end, wherein at least a portion of said insert member adjacent said first end thereof is configured for passage substantially through said uninterrupted bore of said guide, and wherein said insert member has a plurality of thread members on an outer surface thereof adjacent said second end, said thread members corresponding to said thread members within the lumen of said body portion of lockingly positioning the insert member within the bore of the guide; and
   d. means for aligning the guide within the burr hole in the patient's cranium, said alignment means configured for the passage therethrough of at least a lower portion of said guide so as to permit engagement of said guide within said burr hole,
   wherein an instrument inserted through said platform enters the interior of the patient's cranium at an angle of substantially 90° to a plane tangent at the cranium at the burr hole.

37. A surgical work platform for facilitating insertion of an instrument into the cranium of a patient through a burr hole previously formed in said cranium, without causing undue injury to underlying tissue therein, said platform comprising:
   a. a guide for directing the instrument through the burr hole, said guide comprising
      i. an elongated open tubular member having a first end and a second end, said member defining a lumen extending from said first end to said second end, wherein at least a portion of said member at said first end is configured and adapted for passage through said aperture and into an inner portion of said cranium and wherein at least a portion of an outer surface of said member is threaded;
      ii. a body portion having first and second parallel opposed sides, said first side of said body portion formed integral with said elongated tubular member at said second end thereof, said body portion defining a central lumen extending therethrough from said first side to said second side in alignment with and adjacent to said lumen in said tubular member so as to form, in combination therewith, an uninterrupted bore through said guide, wherein said lumen extending through said body portion has a plurality of thread members located along an inner peripheral circumferential portion thereof to engage corresponding thread members located upon an insert member positionable within said bore; and
      iii. a plurality of flexible slotted tip members formed integral with said elongated open tubular member at a terminal portion of said first end thereof, for stabilizing said guide within the burr hole in the patient's cranium, each said tip member having a substantially perpendicular flange extending outwardly from a terminal portion thereof furtherest removed from said open tubular member;
   b. an adjustable ring-shaped member for securing the guide against the patient's cranium, said ring-shaped member having upper and lower parallel opposed surfaces, defining a central aperture therethrough, extending from said upper surface to said lower surface, said aperture having threaded members located on an inner peripheral surface thereof for engaging said threaded outer surface portion of said elongated open tubular member, thus permitting the platform to be locked in position upon the cranium of the patient by screwing said ring-shaped member in the direction of said cranium;
   c. an elongated tubular insert member having a first end and a second end, said insert member defining a hollow lumen extending from said first end to said second end, wherein at least a portion of said insert member adjacent said first end thereof is configured for passage substantially through said uninterrupted bore of said guide, and wherein said insert member has a plurality of thread members on an outer surface thereof adjacent said second end, said thread members corresponding to said thread members within the lumen of said body portion of lockingly positioning the insert member within the bore of the guide; and
   d. a base member for aligning the guide within the burr hole in the patient's cranium, said base member having an annular body portion with first and second opposed sides configured for the passage therethrough of at least a lower portion of said guide, said base member further comprising a plurality of leg members extending substantially perpendicularly from said first side thereof, said leg members formed integral with said body portion,
   wherein an instrument inserted through said platform enters the interior of the patient's cranium at an angle of substantially 90° to a plane tangent to the cranium at the burr hole.

38. The platform of claim 37, wherein each of said plurality of leg members terminates in a free end, said free ends forming a polygon defining a plane upon said cranium overlaying said burr hole and wherein said guide is aligned with the burr hole at an angle of substantially 90° to said plane.

39. The platform of claim 38 wherein said base member comprises three legs of equal length such that an equilateral triangle is formed by the free ends of said legs.

40. A device for facilitating the insertion of an instrument into the cranium of a patient through an aperture previously formed in said cranium, without causing undue injury to underlying tissue therein, said device comprising:
   a. guide means for directing said instrument through said aperture, said guide means comprising
      i. an elongated open tubular member having a first end and a second end, said member defining a lumen extending from said first end to said second end, wherein at least a portion of said member at said first end is configured and adapted for passage through said aperture and into an inner portion of said cranium;
      ii. means formed integral with said open tubular body member, at said first and thereof, for stabilizing said guide means within said aperture in said cranium; and
      iii. a body portion having first and second parallel opposed sides, said first side of said body portion formed integral with said elongated open tubular member at said second end thereof, said body portion defining a lumen extending therethrough from said first side to said second side, in alignment with and adjacent to said lumen in said tubular member, to form, in combination, therewith, and uninterrupted bore through said guide means,
   wherein said second side of said body portion comprises a plurality of marking means to facilitate alignment of said instrument within said cranium upon the insertion thereof through the lumen of said guide means;
   b. adjustable means for locking said guide means against said cranium, said locking means defining an aperture therethrough, and configured and adapted for engaging said outer surface portion of said tubular member; and
   c. a base member for aligning said guide means within said aperture to said cranium, said base member having an annular body portion with first and second opposed sides and a plurality of leg members extending substantially perpendicularly from said first side thereof, said leg members formed integral with said body portion, said base member being configured for the passage therethrough of at least a portion of said guide means, wherein instruments inserted through said device enter the interior of the cranium at an angle of substantially 90° to a plane tangent to the cranium at the aperture.

41. The device of claim 40 wherein said marking means are each located the same distance apart along a peripheral circumferential portion of said second side of said body portion.

42. The device of claim 41 wherein each said marking means is located 15 degrees apart from either adjacent one of said marking means.

43. A surgical work platform for facilitating insertion of an instrument into the cranium of a patient through a burr hole previously formed in said cranium, without causing undue injury to underlying tissue therein, said platform comprising:

a. a guide for directing the instrument through the burr hole, said guide comprising
   i. an elongated open tubular member having a first end and a second end, said member defining a lumen extending from said first end to said second end, wherein at least a portion of said member at said first end is configured and adapted for passage through said aperture and into an inner portion of said cranium and wherein at least a portion of an outer surface of said member is threaded for engagement with separate locking means;
   ii. a body portion having first and second parallel opposed sides, said first side of said body portion formed integral with said elongated tubular member at said second end thereof, said body portion defining a central lumen extending therethrough from said first side to said second side in alignment with and adjacent to said lumen in said tubular member so as to form, in combination therewith, an uninterrupted bore through said guide, wherein the second side of said body portion comprises a plurality of graduated alignment markings located along a peripheral circumferential portion thereof, each said marking being located about 15 degrees apart from an adjacent marking on either side thereof, and wherein said lumen extending through said body portion has a plurality of thread members located along an inner peripheral circumferential portion thereof to engage corresponding thread members located upon an insert member positionable within said bore; and
   iii. a plurality of flexible slotted tip members formed integral with said elongated open tubular member at a terminal portion of said first end thereof, for stabilizing said guide within the burr hole in the patient's cranium, each said tip member having a substantially perpendicular flange extending outwardly from a terminal portion thereof furtherest removed from said open tubular member;
 b. adjustable locking means for securing the guide against the patient's cranium, said locking means defining a central lumen configured for engaging said threaded outer portion of said elongated open tubular member;
 c. an elongated tubular insert member having a first end and a second end, said insert member defining a hollow lumen extending from said first end to said second end, wherein at least a portion of said insert member adjacent said first end thereof is configured for passage substantially through said uninterrupted bore of said guide, and wherein said insert member has a plurality of thread members on an outer surface thereof adjacent said second end, said thread members corresponding to said thread members within the lumen of said body portion for lockingly positioning the insert member within the bore of the guide; and
 d. a base member for aligning the guide within the burr hole in the patient's cranium, said base member having an annular body portion with first and second opposed sides and a plurality of leg members extending substantially perpendicularly from said first side thereof, said leg members formed integral with said body portion, said base member being configured for the passage therethrough of at least a lower portion of said guide so as to permit engagement of said guide within said burr hole, wherein an instrument inserted through said platform enters the interior of the patient's cranium at an angle of substantially 90° to a plane tangent at the cranium at the burr hole.

44. A surgical work platform for facilitating insertion of an instrument into the cranium of a patient through a burr hole previously formed in said cranium, without causing undue injury to underlying tissue therein, said platform comprising:

a. a guide for directing the instrument through the burr hole, said guide comprising
   i. an elongated open tubular member having a first end and a second end, said member defining a lumen extending from said first end to said second end, wherein at least a portion of said member at said first end is configured and adapted for passage through said aperture and into an inner portion of said cranium and wherein at least a portion of an outer surface of said member is threaded for engagement with separate locking means;
   ii. a body portion having first and second parallel opposed sides, said first side of said body portion formed integral with said elongated tubular member at said second end thereof, said body portion defining a central lumen extending therethrough from said first side to said second side in alignment with and adjacent to said lumen in said tubular member so as to form, in combination therewith, an uninterrupted bore through said guide wherein said lumen extending through said body portion has a plurality of thread members located along an inner peripheral circumferential portion thereof to engage corresponding thread members located upon an insert member positionable within said bore; and
   iii. a plurality of flexible slotted tip members formed integral with said elongated open tubular member at a terminal portion of said first end thereof, for stabilizing said guide within the burr hole in the patient's cranium, each said tip member having a substantially perpendicular flange extending outwardly from a terminal portion thereof furtherest removed from said open tubular member;
 b. a ring-shaped locking member having upper and lower parallel opposed surfaces, defining a central aperture therethrough, extending from said upper surface to said lower surface, said aperture having threaded members located on an inner peripheral surface thereof for engaging said corresponding threaded members located upon the outer surface portion of said elongated open tubular member, thus permitting said platform to be locked in position upon the cranium of the patient by screwing said ring-shaped member in the direction of said alignment means;

c. an elongated tubular insert member having a first end and a second end, said insert member defining a hollow lumen extending from said first end to said second end, wherein at least a portion of said insert member adjacent said first end thereof is configured for passage substantially through said interrupted bore of said guide, and wherein said insert member has a plurality of thread members on an outer surface thereof adjacent said second end, said thread members corresponding to said thread members within the lumen of said body portion for lockingly positioning the insert member within the bore of the guide; and d. a base member for aligning the guide within the burr hole in the patient's cranium, said base member having an annular body portion with first and second opposed sides and a plurality of leg members extending substantially perpendicularly from said first side thereof, said leg members formed integral with said body portion, wherein each of said plurality of legs terminates in a free end, said free ends forming a polygon defining a plane upon said cranium overlaying said burr hole and wherein said guide is aligned with the burr hole at an angle of substantially 90° to said plane, said base member being configured for the passage therethrough of at least a lower portion of said guide so as to permit engagement of said guide within said burr hole, wherein an instrument inserted through said platform enters the interior of the patient's cranium at an angle of substantially 90° to a plane tangent to the cranium at the burr hole.

45. The platform of claim 44 wherein said base member comprises three legs of equal length such that an equilateral triangle is formed by the free ends of said legs.

46. A method for inserting a medical instrument through a previously prepared aperture in a patient's cranium, said method comprising:

a. assembling upon the cranium of a patient a device for facilitating the insertion of an instrument into said cranium through an aperture previously formed therein, without causing undue injury to underlying tissue therein, said device comprising 1. guide means for directing said instrument through said aperture, said guide means comprising
   i. an elongated open tubular member having a first end and a second end, said member defining a lumen extending from said first end to said second end, wherein at least a portion of said member at said first end is configured and adapted for passage through said aperture and into an inner portion of said cranium; and
   ii. means formed integral with said open tubular body member, at said first and thereof, for stabilizing said guide means within said aperture in said cranium;
2. adjustable means for locking said guide means against said cranium, said locking means defining an aperture therethrough, and configured and adapted for engaging said outer surface portion of said tubular member; and
3. a base member for aligning said guide means within said aperture in said cranium, said base member having an annular body portion with first and second opposed sides and a plurality of leg members extending substantially perpendicularly from said first side thereof, said leg members formed integral with said body portion, said base member being configured for the passage therethrough of at least a portion of said guide means, wherein said device is assembled by 1. forming an aperture through said cranium at an angle of substantially 90° to a plane tangent to the cranium at the aperture;
2. deburring the aperture to remove any loose bone chips therefrom;
3. positioning said base member above said aperture on the surface of the cranium;
4. inserting said guide means through said aperture on the surface of the cranium; and
5. engaging an elongated insert member having a central lumen within an uninterrupted bore defined by said guide means; and b. inserting said medical instrument through said device and into an interior portion of said cranium at an angle of substantially 90° to a plane tangent to said cranium at said aperture.

* * * * *